United States Patent
Desbois et al.

(10) Patent No.: US 7,288,612 B2
(45) Date of Patent: *Oct. 30, 2007

(54) INITIATOR COMPOSITION AND METHOD FOR ANIONIC POLYMERISATION

(75) Inventors: Philippe Desbois, Maikammer (DE); Christian Schade, Ludwigshafen (DE); Alain Deffieux, Bordeaux (FR); Stephane Menoret, Bordeaux (FR); Jürgen Demeter, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 21 days.

This patent is subject to a terminal disclaimer.

(21) Appl. No.: 10/512,444

(22) PCT Filed: Apr. 15, 2003

(86) PCT No.: PCT/EP03/03900

§ 371 (c)(1), (2), (4) Date: Oct. 25, 2004

(87) PCT Pub. No.: WO03/091296

PCT Pub. Date: Nov. 6, 2003

(65) Prior Publication Data

US 2006/0058177 A1    Mar. 16, 2006

(30) Foreign Application Priority Data

Apr. 23, 2002  (DE)  ................ 102 18 161

(51) Int. Cl.
- C08F 4/48 (2006.01)
- C08F 12/08 (2006.01)
- C08F 36/02 (2006.01)

(52) U.S. Cl. .............. 526/177; 526/173; 526/335; 526/340.2; 526/346; 525/272; 502/154

(58) Field of Classification Search ........... 526/177, 526/346, 173, 335, 340.2; 525/272; 502/154
See application file for complete search history.

(56) References Cited

U.S. PATENT DOCUMENTS

| | | | |
|---|---|---|---|
| 2,915,541 A | 12/1959 | Ziegler et al. | |
| 3,631,006 A * | 12/1971 | Hawkins | ............ 526/177 |
| 3,655,790 A | 4/1972 | Ashby | |
| 3,691,241 A | 9/1972 | Kamienski et al. | |
| 3,716,495 A | 2/1973 | Hsieh | |
| 3,817,955 A | 6/1974 | Kamienski et al. | |
| 6,300,441 B1 | 10/2001 | Schade et al. | |
| 6,303,721 B1 | 10/2001 | Laetsch et al. | |
| 6,444,762 B1 | 9/2002 | Fischer et al. | |
| 2006/0160971 A1 * | 7/2006 | Desbois et al. | ............ 526/173 |

FOREIGN PATENT DOCUMENTS

| | | | |
|---|---|---|---|
| EP | 512 310 | | 11/1992 |
| GB | 947993 | | 1/1964 |
| WO | WO98/07765 | * | 2/1998 |

OTHER PUBLICATIONS

Welch, JACS, vol. 82 (1960), pp. 6000-6005.

* cited by examiner

*Primary Examiner*—Fred Teskin
(74) *Attorney, Agent, or Firm*—Novak Druce & Quigg, LLP

(57) ABSTRACT

The invention relates to an initiator composition for anionic polymerization, comprising at least one alkali metal hydride selected from LiH, NaH, and KH, and at least one organylaluminum compound, and to a process for the anionic polymerization of styrene monomers or of diene monomers using the initiator composition.

10 Claims, No Drawings

INITIATOR COMPOSITION AND METHOD FOR ANIONIC POLYMERISATION

The invention relates to an initiator composition for anionic polymerization, comprising at least one alkali metal hydride selected from LiH, NaH, and KH, and at least one organylaluminum compound.

The invention further relates to a process for preparing the initiator composition, and to a process for the anionic homo- or copolymerization of styrene monomers or of diene monomers in the presence of the initiator composition, and also to the use of the initiator composition for preparing polymers. Finally, the invention relates to the polymers obtainable by the process, to the use of these for producing moldings, films, fibers, or foams, and to the moldings, films, fibers, and foams made from the polymers.

Anionic polymerization generally proceeds very rapidly, and the considerable amount of heat generated makes control difficult on an industrial scale. If the polymerization temperature is lowered, the result is an excessive rise in viscosity, in particular for concentrated solutions. Reducing the initiator concentration increases the molecular weight of the polymer formed. Control of the reaction via appropriate dilution of the monomers leads to higher requirement for solvent and to low space-time yields.

Various additives to the anionic polymerization initiators, affecting polymerization rate, have therefore been proposed.

The effect of Lewis acids and Lewis bases on the rate of anionic polymerization of styrene has been reported in Welch, Journal of the American Chemical Society, Vol. 82 (1960), pp. 6000-6005. Here it was found that small amounts of Lewis bases, such as ethers and amines, accelerate the n-butyllithium-initiated polymerization of styrene at 30° C. in benzene, whereas Lewis acids, such as alkylzinc and alkylaluminum compounds reduce the polymerization rate or, if used in more than stoichiometric amounts, stop the polymerization.

U.S. Pat. No. 3,655,790 describes organomagnesium-alkali metal hydride complexes $M_n MgR^1 R^2 H_n$ where M=Na, K, Li, Cs; $R^1$ and $R^2$=$C_{3-15}$-alkyl, -aryl, -aralkyl; n=½, 1, 2, 3, and their use as reducing agents and metallizing agents.

U.S. Pat. Nos. 3,691,241 and 3,817,955 disclose a process for the polymerization of various monomers, including butadiene, isoprene, and styrene, using the organomagnesium-alkali metal hydride complexes described in U.S. Pat. No. 3,655,790.

A difference from the metal complexes disclosed above is that neither magnesium nor organylmagnesium compounds is present in the initiator compositions of the invention.

DE-A 19806772 discloses initiator compositions made from an organyl alkali metal compound (i.e. alkyl, aryl, aralkyl alkali metal compound), e.g. sec-butyllithium, and from an organylaluminum compound, e.g. triisobutylaluminum (TIBA), and their use for the polymerization of vinylaromatics and dienes.

U.S. Pat. No. 3,716,495 teaches initiator compositions made from a) organolithium compounds $RLi_x$ where R=$C_{1-20}$-alkyl, -aryl, -cycloalkyl, -alkaryl, or -aralkyl, for example n- or sec-butyllithium, b) organylmetal compounds $R_n M$, where R is as defined above and M=a metal from the groups 2a (alkaline earth metals), 2b (zinc group), and 3a (boron group), e.g. diethylzinc or organylaluminum compounds, and c) polar compounds, such as tetrahydrofuran (THF). They are used for the polymerization of dienes and vinylaromatics.

A disadvantage of the use of initiators which comprise organolithium compounds (organyllithium compounds), for example n-, sec-, or tert-butyllithium, is the high price of the organyllithium compounds, which makes the final polymer product more expensive.

A difference from the two initiator compositions disclosed above is that the initiators of the invention comprise alkali metal hydrides without organyl radicals.

WO-A 98/07765 discloses initiators for anionic polymerization, comprising the organylmetal compounds
$R^1 M^1$ where $M^1$=Li, Na, K
$R^1$=hydrogen, $C_{1-10}$-alkyl, $C_{6-20}$-aryl, $C_{7-20}$-alkyl substituted aryl, and
$R^2_n M^2$ where $M^2$=n-valent element of groups 2a, 2b, or 3a of the Periodic Table,
$R^2$=hydrogen, halogen, $C_{1-20}$-alkyl, $C_{6-20}$-aryl.

A corresponding polymerization process for styrene monomers or diene monomers is also disclosed.

The present invention is a selection invention with respect to WO-A 98/07765, in that hydrogen alone has been selected for $R^1$ and aluminum alone has been selected for $M^2$.

It is an object of the present invention to provide alternate initiator compositions for anionic polymerization (in particular of styrene monomers or diene monomers). An alternate anionic polymerization process for styrenes and dienes was also to be provided. The initiator compositions and the process were to have better cost-effectiveness than the processes of the prior art.

We have found that this object is achieved by means of the initiator compositions, processes, and uses mentioned at the outset. The abovementioned polymers and their use have also been found, as have the moldings, films, fibers, and foams.

Preferred embodiments of the invention are given in the subclaims.

The initiator composition of the invention comprises at least one alkali metal hydride selected from lithium hydride LiH, sodium hydride NaH, and potassium hydride KH, and at least one organylaluminum compound (organoaluminum compound).

It is possible that the alkali metal hydride acts as initiator for anionic polymerization, e.g. of styrene monomers, insofar as it is present in solution in the solvent (usually non-polar, inert hydrocarbons). The organylaluminum compound improves the solubility of the alkali metal hydride in the solvent, possibly by complexing, and thus improves the activity of the alkali metal hydride. In addition, the Al organyl compound slows the rate of polymerization of the monomers ("retarder" action).

The alkali metal hydrides may be prepared in a known manner from the corresponding metals and gaseous hydrogen at superatmospheric pressure and elevated temperature. However, they are also available in the chemicals market, for example in the form of pure solid or a suspended in a solvent.

The amount needed of alkali metal hydride depends inter alia on the desired molecular weight (molar mass) of the polymer to be prepared, on the type and amount of organylaluminum compounds used, and on the polymerization temperature. The amount used is generally from 0.0001 to 10 mol %, preferably from 0.001 to 1 mol %, and particularly preferably from 0.01 to 0.2 mol %, of alkali metal hydride, based on the total amount of monomers used.

Organylaluminum compounds which may be used are monoorganyl compounds $RH_2Al$, diorganyl compounds $R_2HAl$, and —preferably—triorganyl compounds $R_3Al$. These radicals R may be identical or different and each independently of one another is hydrogen, halogen, $C_1$-$C_{20}$-alkyl, $C_6$-$C_{20}$-aryl, or $C_7$-$C_{20}$-alkyl-substituted aryl. Preferred organylaluminum compounds are the trialkylaluminum compounds, such as triethylaluminum, triisobutylaluminum, tri-n-butylaluminum, triisopropylaluminum, tri-n-hexylaluminum. It is particularly preferable to use triisobutylaluminum (TIBA).

The organylaluminum compounds used may also be those produced by partial or complete hydrolysis, alcoholysis, aminolysis, or oxidation of alkyl- or arylaluminum compounds, or those which bear alcoholate, thiolate, amide, imide, or phosphide groups. Examples are diethylaluminum (N,N-dibutylamide), diethylaluminum ethoxide, diisobutylaluminum ethoxide, diisobutyl-(2,6-di-tert-butyl-4-methylphenoxy)aluminum (CAS No. 56252-56-3), methylaluminoxane, isobutylated methylaluminoxane, isobutylaluminoxane, tetraisobutyldialuminoxane, and bis(diisobutyl)aluminum oxide.

The organylaluminum compounds are obtainable in a manner known per se or may be purchased in the form of commercially available products.

The amount needed of organylaluminum compound depends inter alia on the type and amount of alkali metal hydrides used, and on the polymerization temperature. The amount used is usually from 0.0001 to 10 mol %, preferably from 0.001 to 1 mol %, and particularly preferably from 0.01 to 0.2 mol %, of organylaluminum compound, based on the total amount of monomers used.

The molar ratio of alkali metal hydride (initiator) to organylaluminum compound (retarder) may vary within wide limits.

It depends, for example, on the desired retardant action, the polymerization temperature, the nature and amount (concentration) of the monomers used, and the desired molecular weight of the polymer.

It is useful to express the molar ratio mentioned as a molar ratio of aluminum to alkali metal, Al/Li or Al/Na, or Al/K. In one preferred embodiment it is from 0.01:1 to 5:1, particularly preferably from 0.1:1 to 2:1, and in particular from 0.5:1 to 1:1.

To prepare the initiator composition, it is usual to mix the alkali metal hydride and the organylaluminum compound, preferably with concomitant use of a solvent or suspension medium (depending on the solubility of the alkali metal hydride or of the organylaluminum compound, the term solvent being used below for brevity).

Particularly suitable solvents are inert hydrocarbons, more specifically aliphatic, cycloaliphatic, or aromatic hydrocarbons, such as cyclohexane, methylcyclohexane, pentane, hexane, heptane, isooctane, benzene, toluene, xylene, ethylbenzene, decalin, or paraffin oil, or a mixture of these. Toluene is particularly preferred.

In one preferred embodiment, the alkali metal hydride is used as it stands, i.e. as a dry solid. In another preferred embodiment, the organylaluminum compound is used in solution in an inert hydrocarbon, e.g. toluene.

The temperature during the preparation of the initiator composition depends on the concentration, on the nature of the metal compounds, and on the solvent. The entire temperature range between the freezing point and boiling point of the mixture is usually suitable. It is advantageous to operate in the range from 0 to 250° C., preferably in the range from 20 to 200° C.

The holding or aging of the freshly prepared initiator composition is important for reproducible use in anionic polymerization. Experiments have shown that initiator components which are used separately from one another or are mixed only briefly prior to the initiation of the polymerization bring about polymerization conditions and polymer properties which have poor reproducibility. The aging process observed is probably attributable to complexing of the metal compounds, which proceeds more slowly that the mixing procedure.

An aging time of about 2 minutes is generally sufficient for the range of concentration and temperature given above. The homogeneous mixture is preferably allowed to age for at least 5 minutes, in particular at least 20 minutes. However, if the homogeneous mixture is allowed to age for a number of hours, e.g. from 1 to 480 hours, this again does not generally have an adverse effect.

Another possibility is that styrene is also added to the initiator composition. In this case the result is an oligomeric polystyryl anion having the organyl metal compounds complexed at its chain end. It is preferable to use amounts of styrene in the range from 10 to 1000 mol %, based on the alkali metal hydride.

The initiator components may be mixed in any mixing assembly, preferably in those which can be charged with an inert gas. Examples of suitable assemblies are stirred reactors with an anchor stirrer or vibrating vessels. Heatable tubes with static mixing elements are particularly suitable for continuous preparation. The mixing procedure is needed for homogeneous mixing of the initiator components. Mixing can, but need not, continue while the mixture is allowed to age. The mixture may also be allowed to age in a stirred tank through which materials flow continuously, or in a tube section, the volume of which together with the throughput rate determines the aging time.

The invention therefore also provides a process for preparing an initiator composition comprising at least one alkali metal hydride selected from LiH, NaH, and KH, and at least one organylaluminum compound, where the alkali metal hydride and the organylaluminum compound suspended or dissolved in an inert hydrocarbon are mixed and the mixture is aged at from 0 to 120° C. for at least 2 minutes.

The invention also provides a process for the anionic homo- or copolymerization of styrene monomers or of diene monomers or mixtures of these in the presence of an initiator composition, where the initiator composition comprises at least one alkali metal hydride selected from LiH, NaH, and KH, and at least one organylaluminum compound. This is therefore a process in which the initiator composition of the invention is used.

Suitable styrene monomers are any of the vinylaromatic monomers, e.g. styrene, p-methylstyrene, p-tert-butylstyrene, ethylstyrene, vinylstyrene, vinylnaphthalene, and 1,1-diphenylethylene. It is preferable to use styrene.

Examples of diene monomers which may be used are 1,3-butadiene, 2,3-dimethylbutadiene, 1,3-pentadiene, 1,3-hexadiene, isoprene, and piperylene. 1,3-Butadiene and isoprene are preferred, in particular 1,3-butadiene (the abbreviated name butadiene being used below). It is advantageous for the monomers used to have the purity typically required for the process, i.e. troublesome impurities such as residual moisture, polar substances, and oxygen are removed immediately prior to polymerization in a manner known per se.

Use may be made of one type of monomer or of two or more types of monomers, i.e. the process is suitable for homopolymerization and for copolymerization.

During the polymerization reaction, concomitant use may also be made of polar compounds or Lewis bases. Any of the additives known from the literature for anionic polymerization is in principle suitable. The additives generally contain at least one O, N, S or P atom which has a free electron pair. Preference is given to ethers and amines, e.g. tetrahydrofuran, diethyl ether, tetrahydropyran, dioxane, crown ethers, alkylene glycol dialkyl ethers, e.g. ethylene glycol monoethyl ether, ethylene glycol dimethyl ether, N,N,N',N'-tetramethylethylenediamine, N,N,N',N",N"-pentamethyldiethylenetriamine, 1,2-bis(piperidino)ethane, pyridine, N,N,N',N',N",N'-hexamethyltriethylenetriamine, and hexamethylphosphoramide.

The polar compounds or Lewis bases act as an activator and in many cases increase the conversion in the polymerization reaction or raise the reaction rate. They can also control the proportions of the different vinyl linkages in the butadiene polymer or isoprene polymer, see below, and thus affect the microstructure of the rubber. If they increase the reaction rate, their amount is advantageously judged so that the reaction rate of the entire mixture is lower than that in a mixture which uses no addition of the retarding components. To this end, use is made of less than 500 mol %, preferably less than 200 mol %, and in particular less than 100 mol %, of the polar compound or Lewis base, based on the initiator composition.

The process of the invention may be carried out in the presence (solution polymerization) or absence (bulk polymerization) of a solvent. With no solvent, operations are generally carried out at above 100° C., these being temperatures at which polymer melts may also be handled.

Suitable solvents for the anionic polymerization are the usual aliphatic, cycloaliphatic, or aromatic hydrocarbons having from 4 to 12 carbon atoms, for example pentane, hexane, heptane, cyclohexane, methylcyclohexane, isooctane, decalin, benzene, alkylbenzenes, such as toluene, xylene, ethylbenzene, or cumeme, or a suitable mixture. The solvent should be of the purity typically required for the process. To remove substances with active protons, it may be dried over aluminum oxide or molecular sieve, for example, and/or distilled prior to use. The solvent from the process is preferably reused after condensation of the solvent vapors and the purification mentioned.

In solution polymerization, operations are usually carried out at from 0 to 250° C., preferably from 20 to 200° C.

It is possible to adjust the retardant action within wide temperature ranges via the selection of composition and amount of the organylaluminum compounds. For example, it is even possible to use starting monomer concentrations in the range from 50 to 100 percent by volume, in particular from 70 to 100 percent by volume, for the polymerization. These give high-viscosity polymer solutions and, at least for relatively high conversions, demand relatively high temperatures.

Once the polymerization has ended, the living polymer chains may be capped by a chain terminator. Suitable chain terminators are substances with active protons or Lewis acids, examples being water, alcohols, such as methanol or isopropanol, aliphatic or aromatic carboxylic acids, and also inorganic acids, such as carbonic acid or boric acid.

The process of the invention may be carried out in any reactor which can withstand pressure and heat, and in principle it is possible to use back-mixing or non-back-mixing reactors (i.e. reactors with stirred tank behavior or tubular reactor behavior).

Depending on the selection of the initiator concentration and initiator composition, of the specific process sequence used, and other parameters, such as temperature and, if desired, temperature program, the process leads to polymers with high or low molecular weight. Examples of suitable equipment are stirred tanks, tower reactors, loop reactors, and also tubular reactors or tube-bundle reactors, with or without internals. Internals may be static or movable internals.

Besides the polymerization process described above and the use of the initiator composition for preparing polymers, the invention also provides the polymers obtainable by the polymerization process.

Examples of these polymers are homopolymers, such as polystyrene (PS or GPPS for general-purpose polystyrene), polybutadiene (PB), and polyisoprene (PI). Examples of copolymers are high impact polystyrene (HIPS) and styrene-butadiene block copolymers (S-B polymers, which can be abbreviated to SBP).

The process of the invention therefore permits the preparation of thermoplastic molding compositions (e.g. PS or HIPS) and of elastomers (e.g. PB, PI, SBP).

The styrene-butadiene block copolymers of the invention may be linear two-block S-B copolymers or three-block S-B-S or B-S-B copolymers, for example (S=styrene block, B=butadiene block), these being obtained via anionic polymerization by the process of the invention. The way in which the block structure arises is essentially that styrene alone is first polymerized anionically, giving a styrene block. Once the styrene monomers have been consumed the monomer is changed by feeding monomeric butadiene and polymerizing this anionically to give a butadiene block ("sequential polymerization"). The resultant two-block S-B polymer may be polymerized to give a three-block S-B-S polymer by again changing the monomer to styrene, if desired. The same principle applies for B-S-B three-block copolymers.

In the three-block copolymers, the two styrene blocks may be of the same size (same molecular weight, i.e. symmetrical $S_1$-B-$S_1$ structure) or of different size (different molecular weight, i.e. asymmetrical $S_1$-B-$S_2$ structure). The same principle applies for the two butadiene blocks of the B-S-B block copolymers. Block sequences S—S-B or $S_1$—$S_2$-B, or S-B-B or S-$B_1$-$B_2$ are, of course, also possible. The indices above represent the block sizes (block lengths or molecular weights). The block sizes depend on the amounts of monomers used and the polymerization conditions, for example.

Instead of the elastomeric "soft" butadiene blocks B, or in addition to the blocks B, there may also be B/S blocks. These are likewise soft and contain butadiene and styrene, for example randomly distributed or in the form of a tapered structure (tapered=gradient from styrene-rich to styrene-poor or vice versa). If the block copolymer contains two or more B/S blocks, the absolute amounts, and the relative proportions, of styrene and butadiene in each of the B/S blocks may be identical or different (giving different blocks $(B/S)_1$, $(B/S)_2$, etc.).

Other suitable styrene-butadiene block copolymers are four-block and polyblock copolymers.

The block copolymers mentioned may have a linear structure (described above). However, branched or star-shaped structures are also possible and are preferred for some applications. Branched block copolymers are obtained in a known manner, e.g. by graft reactions of polymeric "side branches" onto a main polymer chain.

An example of a method for obtaining star-shaped block copolymers is reaction of the living anionic chain ends with an at least bifunctional coupling agent. Examples of descriptions of these coupling agents are found in U.S. Pat. Nos. 3,985,830, 3,280,084, 3,637,554, and 4,091,053. Preference is given to epoxidized glycerides (e.g. epoxidized linseed-oil or soy oil), silicon halides, such as $SiCl_4$, or divinylbenzene, or else polyfunctional aldehydes, ketones, esters, anhydrides, or epoxides. Other compounds suitable specifically for dimerization are dichlorodialkylsilanes, dialdehydes, such as terephthalaldehyde, and esters, such as ethyl formate. Coupling of identical or different polymer chains may be used to prepare symmetrical or asymmetrical star structures, i.e. each of the branches in the star may be identical or different, and in particular may contain different blocks S, B, B/S, or different block sequences. Further details relating to star-shaped block copolymers can be found in WO-A 00/58380, for example.

The monomer names styrene and butadiene used above are given by way of example but also include other vinylaromatics and dienes, respectively.

The styrene-butadiene block copolymers are in accordance with the invention as long as at least one block has been prepared by the process of the invention. This means that it is not necessary for all of the blocks to be prepared by the process of the invention. For example, it is possible for at least one block to be polymerized using an initiator composition of the invention comprising alkali metal hydride and organylaluminum compound and for one or more other blocks of the same block copolymer to be prepared by another process not of the invention, for example using organolithium compounds or organomagnesium compounds.

The high impact polystyrene (HIPS) of the invention comprises, besides the polystyrene matrix, a rubber component, such as polybutadiene, polyisoprene, or —preferably—styrene-butadiene block copolymers.

The rubber components here may be prepared by the process of the invention or else by processes of the prior art, e.g. by anionic polymerization using organolithium compounds, or by free-radical polymerization.

In the case of rubbers prepared by anionic polymerization, the rubber is generally present in solution in a solvent or in monomeric styrene. In the process of the invention, the rubbers do not need to be removed from the solvent (although this is possible). Instead, the solution of the rubber with solvent may be used directly for further processing to give the HIPS.

To this end, monomeric styrene and the initiator composition of the invention are added to the rubber solution which, where appropriate, has previously been permitted to complete its reaction by way of addition of chain terminator, and the mixture is polymerized anionically by the process of the invention, i.e. styrene is polymerized in the presence of the rubber.

Polymers of the invention include an HIPS comprising rubber prepared according to the invention, where the styrene matrix has been polymerized by a process other than the inventive process in the presence of the rubber.

The HIPS of the invention therefore encompasses HIPS polymers in which either the rubber component or the styrene matrix or both constituents have been prepared by the process of the invention.

According to the invention, particular preference is given to impact-resistant polystyrene molding compositions in which the rubber present comprises a) a styrene-butadiene two-block $S_1$-$B_1$ copolymer with styrene content of from 30 to 70% by weight, preferably from 40 to 60% by weight, based on the two-block copolymer, or b) a mixture of the two-block copolymer described in a) with a second styrene-butadiene two-block $S_2$-$B_2$ copolymer with styrene content of from 10 to 50% by weight, preferably from 20 to 40% by weight, based on the two-block copolymer, or c) a mixture of the two-block copolymer described in a) with a styrene-butadiene-styrene three-block S-B-S copolymer with styrene content of from 5 to 75% by weight, preferably from 20 to 50% by weight, based on the three-block copolymer. The three-block copolymer used particularly preferably comprises a $S_1$-B-$S_2$ polymer in which the styrene block $S_1$ has a weight-average molecular weight Mw of from 20 000 to 200 000, preferably from 50 000 to 120 000, the butadiene block B has a Mw of from 30 000 to 300 000, preferably from 100 000 to 200 000, and the styrene block $S_2$ has a Mw of from 1000 to 100 000, preferably from 5000 to 30 000.

In the case of the styrene-butadiene block copolymers, in the polybutadiene, and in the polyisoprene, the process of the invention moreover permits control of the content of 1,2-vinyl linkages in the polybutadiene or polyisoprene.

Since the mechanical properties of these polymers are also determined by the 1,2-vinyl content of the polybutadiene or polyisoprene, the process therefore permits the preparation of polybutadiene, polyisoprene, and styrene-butadiene block copolymers with tailored properties.

For example, if —not according to the invention— metallic sodium in tetrahydrofuran is used in place of the initiator composition of the invention, a polyisoprene prepared in this way has high content of 1,2-vinyl linkages, giving a different property profile, in particular different mechanical properties.

The polymers of the invention also have low content of residual monomers or residual oligomers. This advantage is particularly significant in the case of the styrene-containing polymers PS, HIPS, and P-S-B, since the low content of residual styrene monomers and styrene oligomers makes it unnecessary to carry out any subsequent devolatilization— e.g. in a vented extruder, associated with higher costs and disadvantageous thermal degradation of the polymer (depolymerization).

The polymers may comprise conventional additives and processing aids, e.g. lubricants, mold-release agents, colorants, e.g. pigments or dyes, flame retardants, antioxidants, light stabilizers, fibrous and pulverulent fillers, fibrous and pulverulent reinforcing agents, or antistats, or else other additives, or a mixture of these.

Examples of suitable lubricants and mold-release agents are stearic acids, stearyl alcohol, stearic esters, stearamides, etal stearates, montan waxes, and those based on polyethylene and polypropylene.

Examples of pigments are titanium dioxide, phthalocyanines, ultramarine blue, iron oxides, and carbon black, and also the other organic pigments. For the purposes of the present invention, dyes are any of the dyes which can be used for the transparent, semitransparent or non-transparent coloring of polymers, in particular those suitable for the coloring of styrene copolymers. Dyes of this type are known to the skilled worker.

Examples of flame retardants which may be used are the halogen-containing or phosphorus-containing compounds known to the skilled worker, magnesium hydroxide, and other commonly used compounds, or a mixture of these.

Examples of suitable antioxidants (heat stabilizers) are sterically hindered phenols, hydroquinones, various substituted representatives of this group, and also mixtures of these. They are commercially available in the form of Topanol® or Irganox®, for example.

Examples of suitable light stabilizers are various substituted resorcinols, salicylates, benzotriazoles, benzophenones, HALS (hindered amine light stabilizers), for example those commercially available in the form of Tinuvin®.

Examples which may be mentioned of fibrous or pulverulent fillers are carbon fibers or glass fibers in the form of glass wovens, glass mats, or glass silk rovings, chopped glass, glass beads, and also wollastonite, particularly preferably glass fibers. When glass fibers are used, these may have been provided with a size and with a coupling agent to improve compatibility with the components of the blend. The glass fibers incorporated may either be short glass fibers or else continuous-filament strands (rovings).

Suitable particulate fillers are carbon black, amorphous silica, magnesium carbonate, chalk, powdered quartz, mica, bentonites, talc, feldspar, or in particular calcium silicates, such as wollastonite, and kaolin.

Examples of suitable antistats are amine derivatives, such as N,N-bis(hydroxyalkyl)alkylamines or -alkyleneamines, polyethylene glycol esters, or glycerol mono- and distearates, and also mixtures of these.

Each of the additives is used in the respective usual amounts, and no further details need therefore be given here.

The molding compositions of the invention may be prepared by mixing processes known per se, for example with melting in an extruder, Banbury mixer, kneader, or on a roll mill or calender.

However, the components may also be mixed "cold", the mixture composed of powder or pellets not being melted and homogenized until processing begins.

It is preferable for the components, where appropriate with the additives mentioned, to be mixed in an extruder or any other mixing apparatus at from 100 to 320° C., with melting, and discharged. It is particularly preferable to use an extruder.

The molding compositions can be used to produce moldings of any type (including semifinished products, films, sheeting, and foams).

The invention therefore also provides the use of the polymers of the invention for producing moldings, films, fibers, and foams, and the moldings, films, fibers, and foams obtainable from the polymers.

EXAMPLES

1. Preparation of Initiator Compositions

The following compounds were used:
lithium hydride (L1H) and sodium hydride (NaH) in solid form from Aldrich,
triisobutylaluminum (TIBA) in the form of ready-to-use 1.0 molar solution in toluene from Aldrich,
toluene from BASF, purified and dried using aluminum oxide.

General Specification for Examples I1 to I6

The alkali metal hydride (type and quantity, see table 1) was added, with stirring at 25° C., to a 1.0 molar solution of TIBA in toluene (amount of solution, see table 1), and the mixture was stirred at 50° C. for 24 hours after addition of toluene (amount, see table 1). This gave an initiator solution which was used without further treatment. The molar ratio of aluminum to alkali metal is given in table 1. Operations were carried out with exclusion of moisture in a glovebox under nitrogen.

TABLE 1

| | Initiator compositions | | | |
|---|---|---|---|---|
| Ex. | Alkali metal hydride | TIBA solution | Toluene | Molar ratio Al/Li or Al/Na |
| I1 | 0.8 g LiH | 40 ml | 960 ml | 0.4:1 |
| I2 | 0.8 g LiH | 70 ml | 930 ml | 0.7:1 |
| I3 | 0.8 g LiH | 90 ml | 910 ml | 0.9:1 |

TABLE 1-continued

Initiator compositions

| Ex. | Alkali metal hydride | TIBA solution | Toluene | Molar ratio Al/Li or Al/Na |
|---|---|---|---|---|
| I4 | 2.4 g NaH | 40 ml | 960 ml | 0.4:1 |
| I5 | 2.4 g NaH | 70 ml | 930 ml | 0.7:1 |
| I6 | 2.4 g NaH | 90 ml | 910 ml | 0.9:1 |

2. Polymerization of Monomers

The compounds used were those given under 1 and the following compounds:

styrene, isoprene, and 1,3-butadiene from BASF, in each case purified and dried using aluminoxane, sec-butyllithium from FMC, methanol and isopropanol from BASF, cyclohexane from BASF, purified and dried using aluminoxane, tetrahydrofuran (THF) from BASF.

All of the polymerizations were carried out with exclusion of moisture in a glovebox under nitrogen.

The molecular weights given below for the polymers (weight-average $M_w$ and number-average $M_n$) were determined by gel permeation chromatography (GPC). The details were as follows: eluent tetrahydrofuran; flow rate 1.2 ml/min; RI or UV detector; three styrene-divinylbenzene gel separating columns (35° C., each 300×8 mm) Polymer Laboratories PLgel Mixed B; calibration using polystyrene standards, polyisoprene standards, or polybutadiene standards, depending on the polymer obtained.

The polydispersity $M_w/M_n$ was calculated from $M_w$ and $M_n$.

The styrene content of the rubbers was determined by evaluating $^1H$ nuclear magnetic resonance (NMR) spectra. The content of 1,2-vinyl linkages in the polybutadiene, in the polyisoprene, or in the butadiene content of the styrene-butadiene block copolymer was determined by $^{13}C$ nuclear magnetic resonance spectroscopy.

2a) Preparation of Polystyrene (PS)

General specification for Examples PS1 to PS9c

One of the initiator solutions prepared previously in examples I1 to I6—or in the case of examples PS8c and PS9c solid initiator—(nature and amount, see table 2) and monomeric styrene (amount, see table 2) were added at 100° C. with stirring to 27 ml of toluene. The fall-off in styrene concentration was followed gravimetrically. After a certain reaction time (see table 2) the polymerization was terminated by adding 1 ml of methanol. Table 2 includes the conversion achieved at that juncture. GPC analysis was used to determine the molecular weights $M_w$ and $M_n$ of the resultant polymer mixture, and the polydispersity $M_w/M_n$ was calculated, see table 2.

TABLE 2

Polystyrene (n.d. not determined, c for comparison)

| Ex | Initiator solution* | Styrene | Reaction time | Conversion | $M_n$ [g/mol] | $M_w/M_n$ |
|---|---|---|---|---|---|---|
| PS1 | 3 ml I1 | 3.5 ml | 5 h | 13% | 1800 | 1.3 |
| PS2 | 3 ml I2 | 3.5 ml | 5 h | 8% | 1000 | 1.2 |
| PS3 | 3 ml I3 | 3.5 ml | 24 h | 15% | 1600 | 1.1 |
| PS4 | 3 ml I3 | 35 ml | 260 h | 95% | 120 000 | 1.2 |
| PS5 | 3 ml I4 | 3.5 ml | 2 h | 82% | 6800 | 1.3 |
| PS6 | 3 ml I5 | 3.5 ml | 2 h | 41% | 6800 | 1.3 |
| PS7 | 3 ml I6 | 3.5 ml | 2 h | 20% | 2000 | 1.2 |
| PS8c | 0.1 g LiH | 3.5 ml | 24 h | <1% | n.d. | n.d. |
| PS9c | 0.1 g NaH | 3.5 ml | 24 h | <1% | n.d. | n.d. |

* examples PS8V and PS9V: solid initiator

The examples show that polystyrenes with low polydispersity and "tailored" molecular weights are obtained.

As expected, the conversion within the series PS1 to PS3 and PS5 to PS7 reduces as organylaluminum compound content in the initiator composition rises (molar ratios Al/Li or Al/Na in examples PS1 and PS5, 0.4:1, PS2 and PS6, 0.7:1, PS3 and PS7, 0.9:1), since the organylaluminum compound acts as retarder. (In the case of example PS3, the higher conversion is due merely to the substantially longer polymerization time, 24 h instead of 5 h).

Example PS4 differs from example PS3 in the larger amount of monomer and the longer reaction time. This method can be used to prepare polymers with high molecular weight.

Comparison of LiH (series PS1 to PS3) with NaH (series PS5 to PS7) reveals that —indeed despite shorter polymerization time—NaH delivers higher conversions and higher molecular weights than LiH.

The comparative examples PS8V and PS9V illustrate that the monomers do not polymerize (no conversion after 24 h) if —not according to the invention—LiH or NaH is used without organylaluminum compound.

2b) Preparation of Polyisoprene (PI)

General Specification for Examples PI1 to PI3

An initiator solution (nature and amount, see table 3) and monomeric isoprene (amount, see table 3) were added, with stirring at 80° C., to 27 ml of toluene. The fall-off in isoprene concentration was followed gravimetrically. After a certain reaction time (see table 3) the polymerization was terminated by adding 1 ml of methanol. Table 3 includes the conversion achieved at that juncture. GPC analysis was used to determine $M_w$ and $M_n$ for the resultant polymer mixture, and the polydispersity was calculated, see table 3. $^{13}C$ NMR was used to determine the proportions of the different vinyl linkages.

TABLE 3

Polyisoprene

| Ex. | Initiator solution | Isoprene | Reaction time | Conversion | $M_n$ [g/mol] | $M_w/M_n$ | Vinyl linkages |
|---|---|---|---|---|---|---|---|
| PI1 | 3 ml I1 | 8 ml | 7 days | 9% | 49 000 | 1.2 | 0% 1,2-vinyl<br>90% 1,3-trans<br>10% 3,4-trans |
| PI2* | 3 ml I1 | 8 ml | 7 days | 76% | 47 000 | 1.2 | 1.6% 1,2-vinyl<br>59.6% 1,4-trans<br>38.9% 3,4-trans |
| PI3 | 2.5 ml I4 | 8 ml | 4 days | 70% | 46 000 | 1.3 | 3.5% 1,2-vinyl<br>43% 1,4-trans<br>53.5% 3,4-trans |

* 10 mol eq/Li of THF were also added to the mixture

The examples show that the polyisoprenes have low polydispersity and tailored molecular weights.

When comparison is made with example PI1, addition of THF in example PI2 permits the proportions of 1,2-, 1,4-trans, and 3,4-trans linkages to be changed, and therefore allows control of the microstructure of the polymer and allows conversion to be increased.

If NaH is used instead of LiH in the initiator composition, higher conversions can be achieved: in example PI3 (using NaH) the conversion is higher, despite considerably shorter polymerization time than in example PI1 (using L1H).

2c) Preparation of Polybutadiene (PB)

Example PB1

3 ml of the initiator solution I5 and sufficient monomeric butadiene to leave a butadiene concentration of 1 mol/l in the mixture were added at 80° C. with stirring to 27 ml of toluene. The fall-off in butadiene concentration was followed gravimetrically. After a reaction time of 2 days the polymerization was terminated by adding 1 ml of methanol. The conversion achieved was 10%. $^{13}$C NMR was used to determine 25% of 1,2-vinyl linkages and 55% of 1,4-trans linkages.

2d) Preparation of Styrene-Butadiene Block Copolymers (SBP)

General Specification for Examples PSB1 to PSB4

Linear block copolymers were prepared by sequential polymerization of styrene and butadiene-styrene mixtures. For this, 500 ml of cyclohexane was stirred, forming an initial charge. Table 4a gives the initiators, monomers, and temperatures used for each of the blocks. The monomers and initiators for the next block were not added until the monomers for the previous block had been consumed. In the case of examples PSB1 and PSB2, the reaction was finally terminated using isopropanol. Table 4b also includes the block structure of the resultant polymers and the proportions by weight of each of the blocks in the block polymer.

In table 4a
I5 is initiator solution from example I5
1 M TIBA is 1.0 molar solution of TIBA in toluene
B is monomeric butadiene
S is monomeric styrene
} is joint addition.

In table 4b:
$S_1$, $S_2$, $S_3$ is a styrene block
$(B/S)_1$, $(B/S)_2$ is a butadiene-styrene block.

TABLE 4a

Styrene-butadiene block copolymers

| Ex. | PSB1 | PSB2 | PSB3 | PSB4 |
|---|---|---|---|---|
| Block 1 | | | | |
| Initiator | 16 ml I5 | 16 ml I5 | 13 ml I5 | 13 ml I5 |
| Monomers | 36 g S | 16 g S | 78 g S | 79 g S |
| Temp. | 100° C. | 100° C. | 100° C. | 100° C. |
| Block 2 | | | | |
| Initiator | 0.3 ml 1 M TIBA | 0.3 ml 1 M TIBA | 45 ml I5 | 45 ml I5 |
| Monomers | 23 g B<br>23 g S } | 23 g B<br>23 g S } | 46 g S | 50 g S |
| Temp. | 120° C. | 120° C. | 120° C. | 120° C. |
| Block 3 | | | | |
| Initiator | — | — | 1 ml 1 M TIBA | 1 ml 1 M TIBA |
| Monomers | 23 g B<br>23 g S } | 23 g B<br>23 g S } | 23 g B<br>23 g S } | 34 g B<br>34 g S } |
| Temp. | 120° C. | 120° C. | 120° C. | 120° C. |
| Block 4 | | | | |
| Initiator | — | — | — | — |
| Monomers | 74 g S | 90 g S | 26 g S | — |
| Temp. | 120° C. | 120° C. | 120° C. | — |

TABLE 4b

Block structure of block copolymers

| Example | Block structure and proportions by weight of blocks in block copolymers [% by weight] |
|---|---|
| PSB1 | $S_1$-$(B/S)_1$-$(B/S)_2$-$S_2$<br>18-23-23-36 |
| PSB2 | $S_1$-$(B/S)_1$-$(B/S)_2$-$S_2$<br>8-23-23-46 |
| PSB3 | $S_1$-$S_2$-$(B/S)_2$-$S_3$<br>39-23-25-13 |
| PSB4 | $S_1$-$S_2$-$(B/S)_2$<br>40-26-34 |

A coupling reaction of the living polymer chains was used to prepare star-shaped block copolymers from the linear block copolymers PSB3 and PSB4, the coupling agent used being epoxidized linseed oil (Edenol® B316 from Henkel). The details of the procedure were as in WO-A 00/58380, examples 6 to 8 on pages 8 to 9.

The examples show that tailored styrene-butadiene block copolymers can be prepared by using appropriate monomer changes and initiators. They can be converted to star-shaped polymers.

It is not necessary here for all of the blocks to be prepared by the process of the invention. Rather, it is possible for one block to be prepared according to the invention using an alkali metal hydride-organylaluminum compound initiator, but for the other block to be prepared by other processes.

2e) Preparation of High Impact Polystyrene (HIPS)

The rubber component used comprised styrene-butadiene block copolymers K, these block copolymers K1, K2 and K3 having been prepared using sec-butyllithium, not according to the invention.

Rubbers K1 and K2: linear butadiene-styrene two-block B-S copolymers dissolved in monomeric styrene The procedure for K1 was as described in DE-A 100 22 504, example K1 on page 4, lines 10-25. The procedure for K2 was as described in DE-A 100 22 504, example K3 on page 4, lines 42-56. The molecular weights $M_w$ for rubber K1 were: polybutadiene block 100 000, polystyrene block 85 000, and for rubber K2 were: polybutadiene block 160 000, polystyrene block 95 000.

Rubber K3: linear styrene-butadiene-styrene three-block S-B-S copolymer dissolved in monomeric styrene The procedure was as described in DE-A 100 22 504, example K5 on page 5, lines 6-20. The molecular weights $M_w$ were: first styrene block 15 000, butadiene block 120 000, second styrene block 70 000.

The HIPS was prepared by continuous polymerization, by polymerizing styrene by the process of the invention in the presence of the above rubbers K1, K2, or K3, in accordance with the following specification.

Examples HI1 to HI3

Styrene and
  for HI1, 653 g/h of rubber solution K1,
  for HI2, 661 g/h of rubber solution K2,
  for HI3, 688 g/h of rubber solution K3
were metered continuously, with stirring, into a 1.9 l stirred tank at
  363 g/h for HI1, 380 g/h for HI2, 361 g/h for HI3,
as were
  initiator I3 for HI1,
  initiator I6 for HI2,
  initiator I3 for HI3
at 35 ml/h, and the mixture was held at 90° C. (HI2: 93° C.). The solids content of the mixture was
  41% by weight for HI1, 43% by weight for HI2, 40% by weight for HI3.

The mixture was conveyed onward to a 4 l tower reactor provided with two heating zones of equal size (internal temperature of first zone 120° C., second zone 160° C.). The discharge from the reactor was treated with 10 g/h of a 10% strength by weight solution of methanol in toluene and then passed through a mixer into which 2.5% by weight, based on the reaction mixture, of mineral oil was metered, and finally passed through a tube section heated to 240° C. Finally, the mixture was depressurized via a controlled-flow valve into a vacuum vessel operated at 10 mbar. The melt was discharged using a conveying screw, and pelletized. Conversion was quantitative.

The polystyrene matrix had a molecular weight $M_w$ of
  168 000 for HI1, 163 000 for HI2, 175 000 for HI3
and a polydispersity $M_w/M_n$ of
  2.8 for HI1, 2.6 for HI2, 2.7 for HI3.

In all three examples the residual monomer content was <5 ppm of styrene and <5 ppm of ethylbenzene.

Example HI4

Example HI3 was repeated with the difference that initiator I6 was used.

4. Properties of HIPS Polymers Prepared

The HIPS pellets were used to produce pressed test specimens to DIN 16770 Part 1 and injection-molded test specimens to ISO 3167.

Yield stress and tensile strain at break were determined to DIN 53455 at 23° C.

Surface gloss was determined by measuring gloss with a micro-TRI-gloss reflectometer from BYK-Gardner, to give reflectometer values to DIN 67530 at observer angle of 60° and 20°.

Hole notch impact strength was determined to DIN 53753 at 23° C. on pressed plaques of 50×6×4 mm with a hole diameter of 3 mm.

The Vicat B heat distortion temperature of the specimens was determined via the Vicat softening point. The Vicat softening point was determined on standard small specimens to DIN 53 460, Method B, using a force of 49.05 N and a temperature rise of 50 K per hour.

The flowability of the molding compositions was determined as melt volume index (MDI) to DIN 53 735 at 260° C. with a load of 5 kg.

Table 5 gives the results.

TABLE 5

| HIPS properties (n.d. not determined) | | | | |
|---|---|---|---|---|
| Example | HI1 | HI2 | HI3 | HI4 |
| Yield stress [N/mm$^2$] | 32.1 | 32.5 | 30.3 | 29.5 |
| Surface gloss [%] at 60°/20° | 91/62 | n.d. | n.d. | n.d. |
| Tensile strain at break [%] | 11 | 23 | 25 | 32 |
| Hole notch impact strength [kJ/m$^2$] | 4.5 | 12.6 | 15.1 | 14.7 |
| MVI [ml/10 min] | 7.6 | 6.4 | 4.8 | 5.2 |
| Vicat B [° C.] | 89 | 91 | 91 | 90 |

The examples confirm that polymers with tailored mechanical and thermal properties can be prepared by the process of the invention.

We claim:

1. A process for the anionic homo- or copolymerization of styrene monomers or of diene monomers or mixtures of these in the presence of an initiator composition, where the initiator composition comprises at least one alkali metal hydride selected from LiH, NaH, and KH, and at least one organylaluminum compound, and the molar ratio of aluminum to alkali metal is from 0.01:1 to 5:1.

2. A process as claimed in claim 1, where triisobutylaluminum is used as organylaluminum compound.

3. A process as claimed in claim 1, where styrene is used as styrene monomer.

4. A process as claimed in claim 1, where butadiene or isoprene or a mixture of these is used as diene monomer.

5. A process as claimed in claim 2, where styrene is used as styrene monomer.

6. A process as claimed in claim 5, where butadiene or isoprene or a mixture of these is used as diene monomer.

7. A process as claimed in claim 2, where butadiene or isoprene or a mixture of these is used as diene monomer.

8. A process as claimed in claim 3, where butadiene or isoprene or a mixture of these is used as diene monomer.

9. An initiator composition for anionic polymerization, comprising LiH and at least one organylaluminum compound, wherein the molar ratio of Al/Li is from 0.4:1 to 0.9:1.

10. An initiator composition for anionic polymerization, comprising NaH and at least one organylaluminum compound, wherein the molar ratio of Al/Na is from 0.4:1 to 0.9:1.

* * * * *